(12) United States Patent
Hosogoe

(10) Patent No.: US 10,492,663 B2
(45) Date of Patent: Dec. 3, 2019

(54) ENDOSCOPE PROVIDED WITH RAISING BASE

(71) Applicant: HOYA CORPORATION, Tokyo (JP)

(72) Inventor: Yoshitsugu Hosogoe, Tokyo (JP)

(73) Assignee: HOYA CORPORATION, Tokyo (JP)

(*) Notice: Subject to any disclaimer, the term of this patent is extended or adjusted under 35 U.S.C. 154(b) by 212 days.

(21) Appl. No.: 15/105,259

(22) PCT Filed: May 25, 2015

(86) PCT No.: PCT/JP2015/064865
§ 371 (c)(1),
(2) Date: Jun. 16, 2016

(87) PCT Pub. No.: WO2015/182540
PCT Pub. Date: Dec. 3, 2015

(65) Prior Publication Data
US 2016/0309993 A1 Oct. 27, 2016

(30) Foreign Application Priority Data

May 26, 2014 (JP) .................................. 2014-108031
May 26, 2014 (JP) .................................. 2014-108032

(51) Int. Cl.
*A61B 1/00* (2006.01)
*A61B 1/273* (2006.01)
*A61B 1/018* (2006.01)

(52) U.S. Cl.
CPC ........ *A61B 1/00098* (2013.01); *A61B 1/0008* (2013.01); *A61B 1/00071* (2013.01);
(Continued)

(58) Field of Classification Search
CPC .............. A61B 1/0008; A61B 1/00087; A61B 1/00089; A61B 1/00098; A61B 1/00101;
(Continued)

(56) References Cited

U.S. PATENT DOCUMENTS

| 2009/0054727 A1 | 2/2009 | Yamaya |
| 2010/0145144 A1 | 6/2010 | Kitano et al. |
| 2016/0206180 A1 | 7/2016 | Hosogoe |

FOREIGN PATENT DOCUMENTS

| JP | 4-50002 Y2 | 11/1992 | |
| JP | 2003305002 A | * 10/2003 | ......... A61B 1/00098 |

(Continued)

OTHER PUBLICATIONS

Search report from PCT/JP2015/064865, dated Aug. 18, 2015.
Official Communication issued in European Patent Office (EPO) Patent Application No. 15 800 616.3, dated Jan. 3, 2018.

*Primary Examiner* — Ryan N Henderson
(74) *Attorney, Agent, or Firm* — Greenblum & Bernstein, P.L.C.

(57) ABSTRACT

An endoscope, provided with a raising base, is provided, which can securely lock a guidewire using the raising base. In the raising base, which is provided with a treatment-tool support groove and a pair of raising-base side walls on the left and right sides thereof, a inner-to-outer communicably-connected groove which communicably connects the inner side of the treatment-tool support groove-with the outer side thereof is formed in at least one of the pair of raising-base side walls; and when the raising base is positioned at the raised position, the guidewire externally projects through the inner-to-outer communicably-connected groove from the treatment-tool support groove to lock-engage with the raising base.

5 Claims, 9 Drawing Sheets

(52) U.S. Cl.
CPC .......... *A61B 1/00112* (2013.01); *A61B 1/018* (2013.01); *A61B 1/273* (2013.01)

(58) Field of Classification Search
CPC ............ A61B 1/00174; A61B 1/00177; A61B 1/00179; A61B 1/00181; A61B 1/273; A61B 1/2733; A61B 1/2736; A61B 1/00183; A61B 1/012; A61B 1/018; A61B 1/00135; A61B 1/00142; A61B 1/00154
See application file for complete search history.

(56) References Cited

FOREIGN PATENT DOCUMENTS

| | | |
|---|---|---|
| JP | 2006-280602 A | 10/2006 |
| JP | 2007-307086 A | 11/2007 |
| JP | 4163438 B2 | 8/2008 |
| JP | 4716594 B2 | 4/2011 |

\* cited by examiner

ENDOSCOPE PROVIDED WITH RAISING BASE

TECHNICAL FIELD

The present invention relates to an endoscope provided with a raising base, by which a treatment tool can be guided, e.g., into pancreatic and bile ducts using a guidewire.

BACKGROUND ART

A side-viewing endoscope in which a treatment tool can be guided into pancreatic and bile ducts using a guidewire is conventionally known in the art. The endoscopes in Patent Literature Nos. 1 and 2 are one example of such an endoscope, and are provided with a raising-base accommodation recess formed in an outer peripheral surface of a distal-end proximity of an insertion portion that extends from a control body, a treatment-tool insertion conduit formed inside the insertion portion so that the distal-end opening and the raising-base accommodation recess are communicably connected with each other, and a raising base, provided in the raising-base accommodation recess, which is rotatable about a rotational shaft that extends in a widthwise direction of the insertion portion. The raising base rotates in accordance with an operation of a controller provided on the control body, and is rotatable about the above-mentioned rotational shaft between a non-raised position, at which the entire raising base is positioned within the raising-base accommodation recess, and a raised position, at which part of the raising base outwardly projects from the raising-base accommodation recess. Furthermore, in Patent Literature No. 1, a wire-engaging groove, having a V-shaped cross section, is formed on the surface of the raising base and is positioned at the distal-end opening side of the treatment-tool insertion conduit when the raising base is positioned at the raised position, and the recessing amount of the V-shaped wire-engaging groove is increasingly greater in a widthwise direction from either side of the raising base toward a central portion of the raising base. Furthermore, in Patent Literature No. 2, a guidewire engaging groove, having an approximate V-shape in a side-elevational view, is formed through a side of the raising base as a through-groove (which extends through a side wall of the raising base).

When an operator carries out a treatment on a pancreatic or bile duct with a treatment tool using the above-described endoscope, first the distal end of the insertion portion of the endoscope is inserted into the duodenum via the patient's mouth, esophagus and stomach, and the aforementioned raising-base accommodation recess is positioned at the close vicinity of the duodenal papilla (to face the raising-base accommodation recess against the duodenal papilla). Thereafter, a flexible catheter is inserted into the opening, at the control-body side, of the treatment-tool insertion conduit of the endoscope, and the distal end of the catheter protrudes from inside the raising-base accommodation recess via the opening at the distal-end side of the treatment-tool insertion conduit. Furthermore, the distal-end proximity of the catheter is brought in contact with the raising base while the distal end of the catheter is made to project toward an outer peripheral side of the insertion portion. Thereafter, the distal end of the catheter is oriented toward the duodenal papilla by rotating the raising base toward the raised position while operating the controller, and the distal end of the catheter is inserted into the duodenal papilla by pushing (moving) the catheter toward the distal end thereof. Subsequently, a contrast agent is injected so that the bile duct or the pancreatic duct can be observed by radioscopy.

Subsequently, the flexible guidewire is inserted inside the catheter from the opening thereof on the control-body side, the distal end of the guidewire is projected from the opening of the catheter at the distal end thereof, and the distal end of the guidewire is inserted into the duodenal papilla. Thereafter, the distal end of the guidewire is inserted until a desired location in the bile duct or the pancreatic duct while the bile duct or the pancreatic duct is observed by radioscopy. Upon indwelling the guidewire thereat, the catheter is pulled out from the treatment-tool insertion conduit (and the patient's lumen) of the endoscope along the guidewire. In this pulling-out operation, first the distal end of the catheter is drawn into the treatment-tool insertion conduit (toward the control body relative to the raising-base accommodation recess) while the base end portion of the guidewire is manually grasped.

Subsequently, in Patent Literature No. 1, the operator rotates the raising base toward the raised position by operating the controller while engaging an intermediate portion of the guidewire into the wire-engaging groove of the raising base. Thereafter, since the intermediate portion of the guidewire is forcibly bent by the wire-engaging groove, the vicinity of the intermediate portion is pushed against at a location opposing the wire-engaging groove of the raising base. Therefore, if a large frictional force between an inner peripheral surface of the catheter and the outer peripheral surface of the guidewire is incurred upon the operator pulling the catheter (which is inserted in the treatment-tool insertion conduit) along the guidewire, the guidewire can be restrained from being unintentionally pulled out from the duodenal papilla. Whereas, when the raised base of the endoscope in Patent Literature No. 2 is rotated toward the raised position, an intermediate portion of the guidewire is forcibly bent by the guidewire engaging groove that is formed through a side of the raising base. Accordingly, the intermediate portion of the guidewire is clasped between the guidewire engaging groove and the edge portion of the opening of the raising-base accommodation recess. Therefore, also with the case of the endoscope of Patent Literature No. 2, if an unintentional pulling force is applied on the guidewire, the guidewire can be restrained from being unintentionally pulled out from the duodenal papilla. Accordingly, in Patent Literature Nos. 1 and 2, it is relatively easy to externally pull out the catheter along the guidewire from the endoscope.

As described above, the operator, with the guidewire engaged with the wire-engaging groove (Patent Literature No. 1) or the guidewire-engaging groove (Patent Literature No. 2), pulls out the catheter protruding from the opening on the control-body side of the treatment-tool insertion conduit of the endoscope, along the guidewire, from the treatment-tool insertion conduit (and the patient's lumen). Subsequently, the distal end (internal space) of the flexible tubular treatment tool is inserted into the treatment-tool insertion conduit along the guidewire (that protrudes from the opening on the control-body side of the treatment-tool insertion conduit and is engaged with the wire-engaging groove (Patent Literature No. 1) or the guidewire-engaging groove (Patent Literature No. 2)), and the distal end of the treatment tool is inserted until reaching a desired location in the bile duct or the pancreatic duct, and a predetermined treatment is performed using the treatment tool. At this stage, since the guidewire is engaged with the wire-engaging groove (Patent Literature No. 1) or the guidewire-engaging groove (Patent Literature No. 2), when a force is exerted on the guidewire by the treatment tool, the distal end of the guidewire can be restrained from unintentionally being moved deeper than the desired location within the bile duct or the pancreatic duct.

Upon the treatment, using the treatment tool, ending, the treatment tool is pulled out from the treatment-tool insertion conduit (and the patient's lumen) of the endoscope along the guidewire. This pulling out of the treatment tool is carried out in the same order as the pulling out of the catheter.

CITATION LIST

Patent Literature

Patent Literature No. 1: Japanese Patent No. 4,716,594
Patent Literature No. 2: Japanese Patent No. 4,163,438

SUMMARY OF THE INVENTION

Technical Problem

However, the endoscopes of Patent Literature Nos. 1 and 2 have the following drawbacks. In the case of Patent Literature No. 1, the manner (angle) by which the intermediate portion of the guidewire is bent by the raising base (wire-engaging groove) changes depending on the positional relationship between the endoscope (raising base) and the duodenal papilla. Therefore, when the endoscope (raising base) and the duodenal papilla are at a certain positional relationship, the intermediate portion of the guidewire is only bent by a slight amount, so that there is a risk of the force that pushes the guidewire against the raising-base accommodation recess deteriorating. If the pushing force deteriorates, when the catheter or the treatment tool is pulled out along the guidewire, there is a risk of the guidewire being unintentionally pulled out from the treatment-tool insertion conduit. If the guidewire were to be pulled out, when another treatment tool, etc., is thereafter is inserted into the duodenal papilla, the guidewire would have to be reinserted into the treatment-tool insertion conduit and the duodenal papilla.

Whereas, in the endoscope of Patent Literature No. 2, the intermediate portion of the guidewire is clasped between the guidewire engaging groove and the edge portion of the opening of the raising-base accommodation recess due to the raising base being rotated toward the raised position, and the clasping force therebetween varies in accordance with the distance between the guidewire engaging groove and the edge portion of the opening of the raising-base accommodation recess (rotational position of the raising base) and the diameter of the guidewire. In other words, the distance between the guidewire engaging groove and the edge portion of the opening of the raising-base accommodation recess (rotational position of the raising base) in order to obtain a suitable clasping force differs for each (diameter of the) guidewire that is used. Accordingly, the rotational position of the raising base needs to the changed in accordance with the (diameter of the) guidewire that is used; however, it is no easy task for the operator to adjust the rotational position of the raising base for each guidewire that is used. Hence, if the guidewire has a small diameter, the distance between the guidewire engaging groove and the edge portion of the opening of the raising-base accommodation recess (rotational position of the raising base) becomes greater than an optimum distance, resulting in a risk of the clasping force against the guidewire, via the guidewire engaging groove and the edge portion of the opening of the raising-base accommodation recess, becoming small. Whereas, if the guidewire has a large diameter, the distance between the guidewire engaging groove and the edge portion of the opening of the raising-base accommodation recess (rotational position of the raising base) becomes less than an optimum distance, resulting in the clasping force becoming excessively greater, so that there is a risk of the intermediate portion (the clasped position) of the guidewire breaking.

An object of the present invention is provide an endoscope provided with a raising base, wherein the raising base can be used to securely lock an intermediate portion of a guidewire to the endoscope without breaking the guidewire.

Solution to Problem

The present invention has been devised by concentrating on exhibiting a guidewire engaging force with only the raising base, by improving on the conventional endoscope (especially the endoscope of Patent Literature No. 2), in which a clasping force was obtained by pushing the guidewire that is guided along the guidewire-engaging groove of the raising base against an inner surface (inner wall surface) of the raising-base accommodation recess when locking the guidewire onto the distal end of the insertion portion.

In the present invention, an endoscope provided with a raising base is provided, including a raising-base accommodation recess formed in a distal-end proximal portion of an insertion portion extending from a control body; a treatment-tool insertion conduit formed in the insertion portion, a distal-end opening of the treatment-tool insertion conduit being communicably connected with the raising-base accommodation recess, and a flexible longitudinal treatment tool and guidewire being insertable the treatment-tool insertion conduit; and a raising base provided in the raising-base accommodation recess, the raising base being rotatable between a non-raised position and a raised position about a rotational shaft extending in a widthwise direction of the insertion portion. The raising base includes a treatment-tool support groove which extends in a direction extending from the insertion portion; a pair of raising-base side walls positioned on either side of the treatment-tool support groove and opposing left and right surfaces of the raising-base accommodation recess in the widthwise direction of the insertion portion; and an inner-to-outer communicably-connected groove provided on at least one of the pair of raising-base side walls, the inner-to-outer communicably-connected groove being formed as a through-groove in a direction of the rotational shaft and formed as a bottomed groove in a direction of depth of the treatment-tool support groove, the inner-to-outer communicably-connected groove communicably connecting an inner side of the treatment-tool support groove with an outer side thereof, wherein the inner-to-outer communicably-connected groove is engagable with the guidewire and is not engagable with the treatment tool. When the raising base is positioned at the raised position, the inner-to-outer communicably-connected groove frictionally engages with the guidewire, with the guidewire guided into the inner-to-outer communicably-connected groove, without causing the guidewire to contact a wall surface of the raising-base accommodation recess.

It is desirable for the inner-to-outer communicably-connected groove to include a pair of mutually opposing groove walls, wherein opposing edges of the mutually opposing groove walls are configured to frictionally engage with the guidewire.

In an embodiment, the pair of raising-base side walls of the raising base define, as a whole, a U-shaped cross section on a portion of the raising-base side walls on which the inner-to-outer communicably-connected groove exists. A base wall of the inner-to-outer communicably-connected groove is positioned above a base portion of the treatment-tool support groove a direction of depth of the treatment-tool support groove.

It is possible for the inner-to-outer communicably-connected groove to be provided on each of the pair of raising-base side walls of the raising base.

It is desirable for an objective lens element to be provided on an outer peripheral surface of the insertion portion. At least part of the inner-to-outer communicably-connected groove is positioned within an observational field-of-view of the objective lens element when the raising base is positioned at the raised position.

Advantageous Effects of the Invention

According to the present invention, upon inserting the guidewire into, e.g., the duodenal papilla and rotating the raising base to the raised position in a state where an intermediate portion of the guidewire has been fed into an inner-to-outer communicably connected groove of the raising base, the inner-to-outer communicably connected groove frictionally engages with the guidewire and can securely lock the guidewire against the raising base (endoscope) without the guidewire contacting a wall surface of the raising-base accommodation recess. In other words, since the raising base can solely lock the guidewire against the endoscope, the guidewire can be locked against the endoscope without any risk of a difference in diameter of the selected guidewire causing insufficient locking force of the guidewire, breakage or debris falling out, etc. Accordingly, when a treatment tool, etc., is inserted into the treatment-tool insertion conduit along the guidewire, it is unlikely for the guidewire to be unintentionally inserted to a deeper position than the desired location within the bile duct or the pancreatic duct. Furthermore, when a treatment tool, etc., that is inserted into the treatment-tool insertion conduit, along the guidewire, is pulled, the risk of the guidewire being unintentionally pulled out from the duodenal papilla is unlikely. Accordingly, it is possible for the treatment tool to be smoothly inserted and removed along the guidewire.

EMBODIMENT

Figure 1:
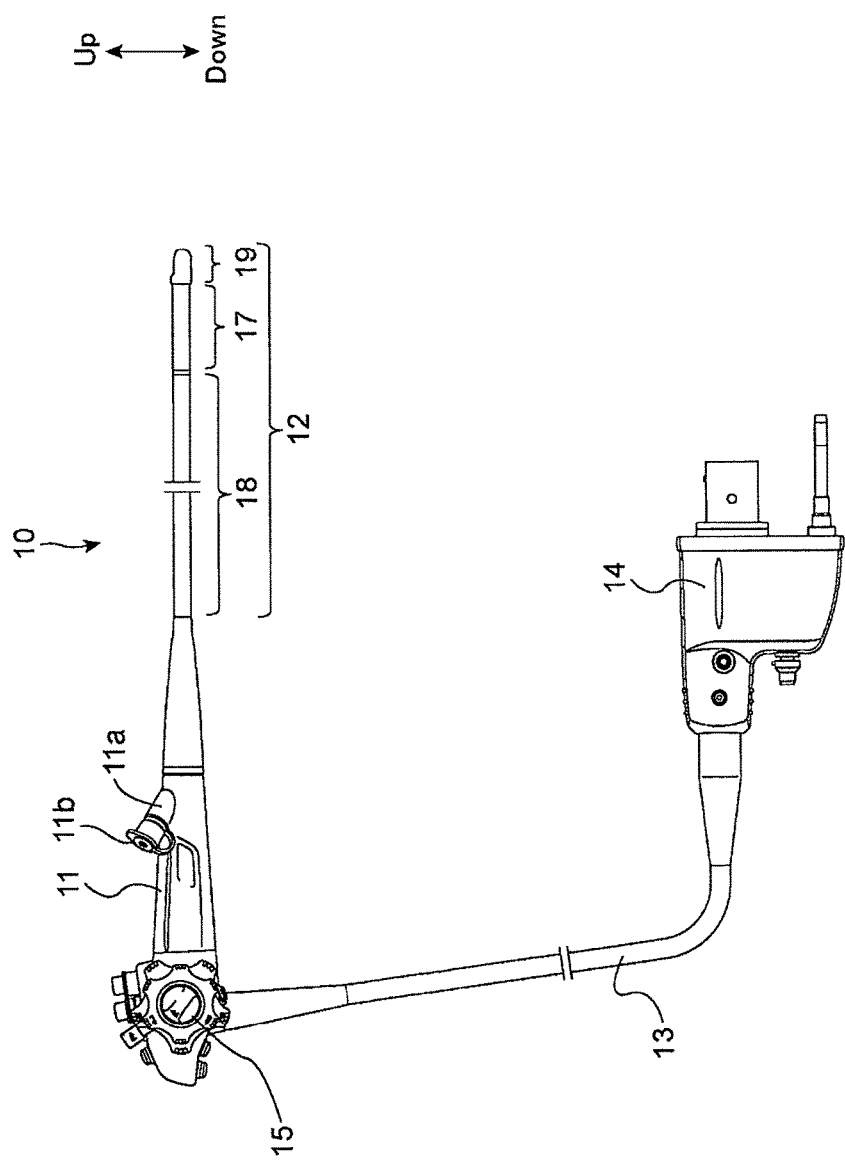
FIG. 1 is an external view of a first embodiment of an endoscope to which the present invention is applied.

A first embodiment of the present invention will be discussed hereinbelow with reference to FIGS. 1 through 12. In the following descriptions, the forward and rearward directions (the distal-end side of the insertion portion 12 of the endoscope 10 is defined as "forward", and the distal side of the universal tube 13 is defined as "rearward"), upward and downward directions, and leftward and rightward directions are based on the directions indicated by the arrows in the drawings. Furthermore, the terms "parallel" and "right angle" do not refer to a geometrical parallel and right angle, but also includes the concept of parallel and right angle when viewed macroscopically.

An endoscope 10 shown in FIG. 1 is a side-viewing endoscope and is provided with a control body 11, an insertion portion 12 which extends forwardly from the control body 11, a universal tube 13 which extends in a direction that is different from that of the control body 11 and the insertion portion 12, and a connector body 14 provided on an end of the universal tube 13. The connector body 14 is connectable to a processor (image processor and light-source apparatus; not shown in the drawings). The processor is connected to a CRT monitor M. A bendable portion 17, which bends in the upward/downward and leftward/rightward directions in accordance with a rotational operation of a bending-control lever 15 provided on the control body 11, is formed on the insertion portion 12. The portion provided on the base side of the bendable portion 17 is configured as a flexible tubular portion 18 that can be bent under its own weight or by being directly controlled by the operator. The portion on the distal-end side of the bendable portion 17 of the insertion portion 12 is configured as a distal-end rigid portion 19. Part of the outer peripheral surface of a front part of the distal-end rigid portion 19 is cut out, and a lens mounting surface 20, formed as a flat surface parallel to the axis of the insertion portion 12, is configured in this cut-out portion. An objective lens element 21 and an illumination lens element 22 are provided on the lens mounting surface 20. The optical axes of the objective lens element 21 and the illumination lens element 22 are parallel to a direction that is orthogonal to the axial direction (forward/rearward direction) of the insertion portion 12 and the axial direction (leftward/rightward direction) of a rotational shaft 25, which will be discussed hereinafter. Furthermore, a raising-base accommodation recess 23 is formed in the distal-end rigid portion 19 at a portion (distal-end proximal portion of the insertion portion 12) adjacent to the lens mounting surface 20. The planar profile of the raising-base accommodation recess 23 is in the form of a rectangle that is longitudinal in the forward/rearward direction (see FIG. 9). A left inner surface 23a and a right inner surface 23b of the raising-base accommodation recess 23 are configured as mutually parallel planar surfaces. An upper edge of the left inner surface 23a is connected to a right side edge of the lens mounting surface 20. An upper edge of the right inner surface 23b is positioned at the same height as that of the left inner surface 23a and the lens mounting surface 20 (see FIGS. 4, 5 and 7). Furthermore, a lower end portion of a rear side of the raising-base accommodation recess 23 is configured as a curved surface 23c (wire contact portion). A flexible light-guide fiber (not shown in the drawings) is provided within each of the connector body 14, the universal tube 13, the control body 11 and the insertion portion 12, and a distal end of the light-guide fiber is connected to the illumination lens element 22. Furthermore, an image sensor (not shown in the drawings), which receives a light bundle (observing image) that transmits through the objective lens element 21, is provided within the distal-end rigid portion 19. A flexible image-signal cable extends rearwardly from the image sensor until reaching inside the connector body 14 through the insides of the insertion portion 12, the control body 11, and the universal tube 13.

As shown in FIG. 1, the front end of the control body 11 is provided with a treatment-tool insertion port protrusion 11a, formed as a tubular portion, for inserting a guidewire W, etc.; the guidewire W is a longitudinal member formed from a flexible and resilient metal. The end-opening of the treatment-tool insertion port protrusion 11a can be opened and closed with a rubber cap 11b. A treatment-tool insertion tube (treatment-tool insertion conduit) 26 is arranged within the insertion portion 12 and extends from the treatment-tool insertion port protrusion 11a toward the distal-end rigid portion 19. The distal-end opening of the treatment-tool insertion tube 26 is communicably connected with the raising-base accommodation recess 23 of the distal-end rigid portion 19, and the guidewire W which is inserted from the treatment-tool insertion port protrusion 11a can protrude into the raising-base accommodation recess 23 from the distal-end opening of the treatment-tool insertion tube 26.

A metal raising base 30, the single-component shape of which is shown in FIG. 3, is accommodated in the raising-base accommodation recess 23. The raising base 30 is provided with a body portion 31 and a supported portion 32, which projects from the body portion 31 and has a narrower width in the leftward/rightward direction than that of the body portion 31.

A pivotal support hole 32a is formed in the supported portion 32 as a leftward/rightward extending through-hole. Furthermore, a wire-locking hole (not shown in the drawings) is formed in the side surface of the body portion 31. The rotational shaft 25, which extends in the leftward/rightward direction (the widthwise direction of the insertion portion 12) is inserted into the pivotal support hole 32a in a fixed manner so that the rotational shaft 25 cannot rotate relative thereto; whereas, left and right end portions of the rotational shaft 25 are respectively inserted into bearing holes (not shown in the drawings) formed in the left inner surface 23a and the right inner surface 23b of the raising-base accommodation recess 23, respectively, and are rotatable relative thereto.

A treatment-tool support groove 33 extending in the forward/rearward direction (the direction of extension of the insertion portion 12) is formed in the body portion 31, and a pair of raising-base side walls 34 are positioned on either side of the treatment-tool support groove 33, with respect to the leftward/rightward direction. The treatment-tool support groove 33 and the raising-base side walls 39 define, as a whole, at a position near the pivotal support hole 32a (rotational shaft 25), a U-shaped groove 33U, having a U-shaped cross section, and define, as a whole, at a position farther from the pivotal support hole 32a (toward the free end of the raising base 30), a V-shaped groove 33V, having a V-shaped cross section. The upper sides of the U-shaped groove 33U and the V-shaped groove are open. A base portion 33a of the treatment-tool support groove 33 is provided and has a linear profile extending in the forward/rearward direction. The base portion 33a and the central axis of the front-end portion of treatment-tool insertion tube 26 are substantially aligned on a common line in a plan view.

An inner-to-outer communicably-connected groove 35 is formed on one of the pair of the raising-base side walls 34 (the left raising-base side 34) of raising base 30. The inner-to-outer communicably-connected groove 35 is formed as a through-hole in a direction parallel, to the pivotal support hole 32a of the raising base 30 and as a bottomed-groove in a depth direction of the treatment-tool support groove 33. The term "communicably-connected" of the inner-to-outer communicably-connected groove 35 refers to "extending through the raising-base side wall 34 to communicably connect the inner side to the outer side of the treatment-tool support groove 33". The width X of the inner-to-outer communicably-connected groove 35 (FIG. 3) is larger than the outer diameter of the guidewire W and is smaller than the outer diameters of the catheter and the treatment tool. In other words, it is possible to guide (engage) the guidewire W into the inner-to-outer communicably-connected groove 35, but it is not possible to guide (engage) the catheter or the treatment tool therein.

The inner-to-outer communicably-connected groove 35 is provided with a mutually opposing (parallel) pair of groove walls 35a and 35b, and a base wall 35c. The groove wall 35a is the wall that is farther from the pivotal support hole 32a (rotational shaft 25) and the groove wall 35b is the wall that is closer to the pivotal support hole 32a. The base wall 35c is positioned at a higher position than that of the base portion 33a of the U-shaped cross section that is defined by the treatment-tool support groove 33 and the raising-base side walls 34, and the base wall 35c is formed as an inclined wall having an increasing depth toward the outer side of the raising-base side wall 34. The groove wall 35a has an inner edge 35a1 (which shares a boundary with the treatment-tool support groove 33) that is closer to the treatment-tool support groove 33 and an outer edge 35a2 (FIG. 3A) that is farther from the treatment-tool support groove 33. The groove wall 35b has an inner edge 35b1 (which shares a boundary with the treatment-tool support groove 33) that is closer to the treatment-tool support groove 33 and an outer edge 35b2 (FIG. 3C) that is farther from the treatment-tool support groove 33.

Figure 8:
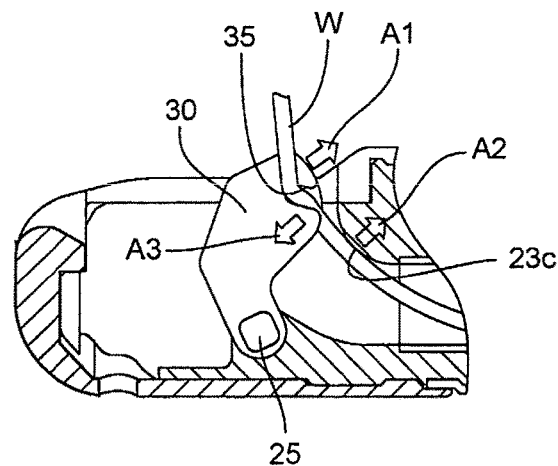
FIG. 8 is a longitudinal cross-sectional view similar to that of FIG. 2, showing a state where the raising base has been rotated to the raised position.
Figure 9:
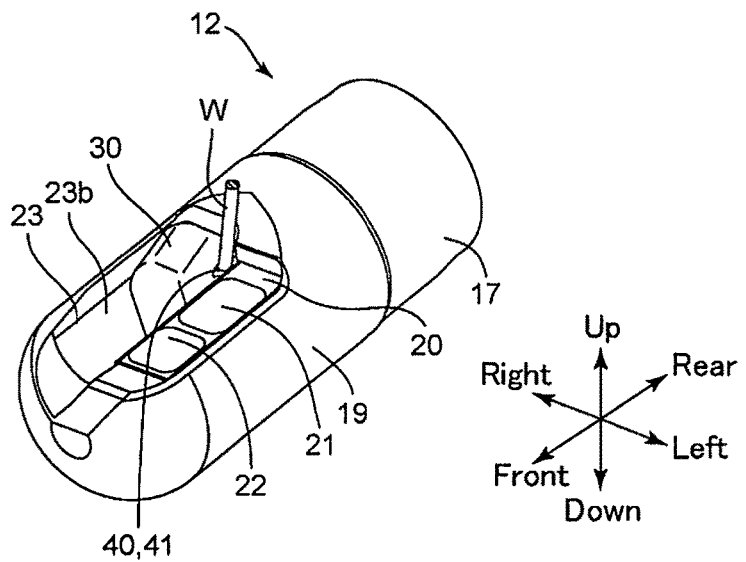
FIG. 9 is a perspective view of the distal end of the insertion portion in the state shown in FIG. 8.

The above-described inner-to-outer communicably-connected groove 35 is substantially orthogonal to a radial direction passing through the center of the rotational shaft 25. At the non-raised position (accommodated position) of the raising base 30, the central axis of the inner-to-outer communicably-connected groove 35 and the lens mounting surface 20 define an angle θ (see the acute angle in FIG. 2). Furthermore, this angle θ gradually reduces during the movement of the raising base 30 from the non-raised position to the raised position to become substantially parallel with the lens mounting surface 20, and thereafter defines a negative angle as shown in FIG. 8 at the maximum raised position of the raising base. Furthermore, when the inner-to-outer communicably-connected groove 35 is parallel with the lens mounting surface 20, at least the groove wall 35a, which is farther from the rotational shaft 25, out of the groove walls 35a and 35b is positioned above the lens mounting surface 20.

Figure 2:
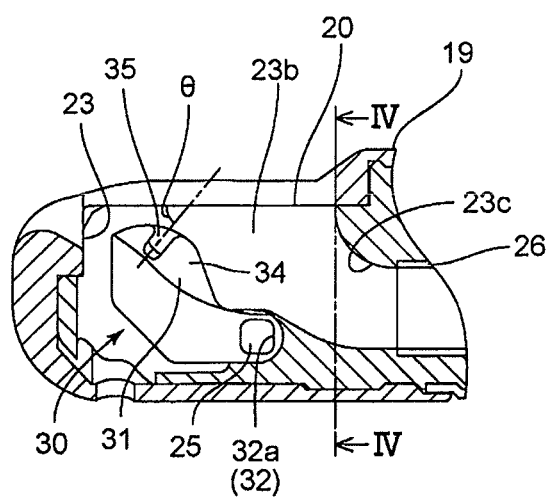
FIG. 2 is a longitudinal cross-sectional view of a distal end (proximity) of an insertion portion when the raising base is positioned at a non-raised position (accommodated position).
Figure 3A:
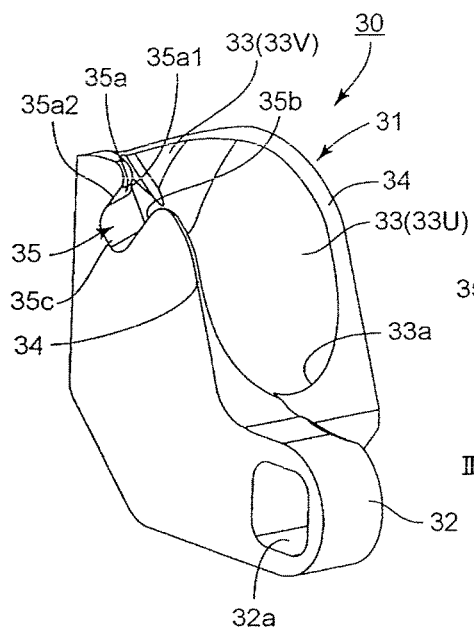
FIG. 3A is a rear perspective view of the shape of the raising base.
Figure 3B:
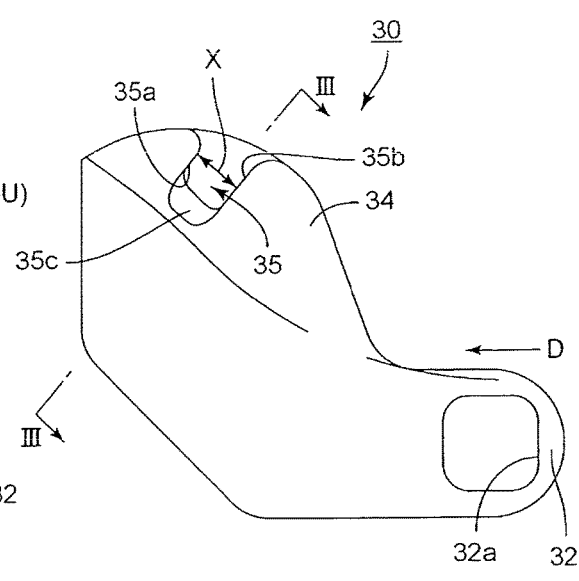
FIG. 3B is a side elevational view of the shape of the raising base.
Figure 3C:
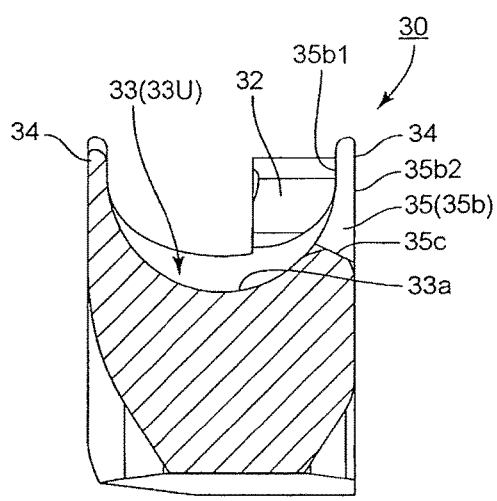
FIG. 3C is a sectional view taken along the III-III line in FIG. 3B.
Figure 3D:
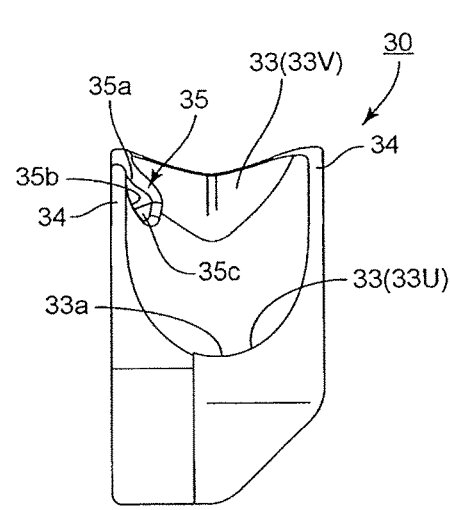
FIG. 3D is a view along the arrow D of FIG. 3B.
Figure 4:
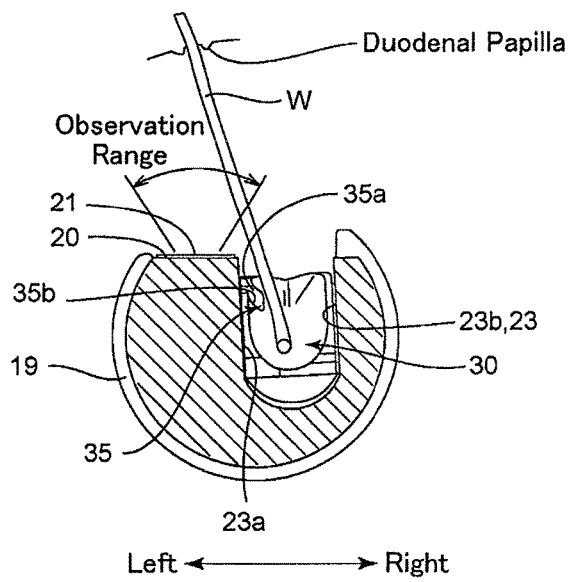
FIG. 4 is a cross-sectional view taken along the IV-IV line in FIG. 2.
Figure 7:
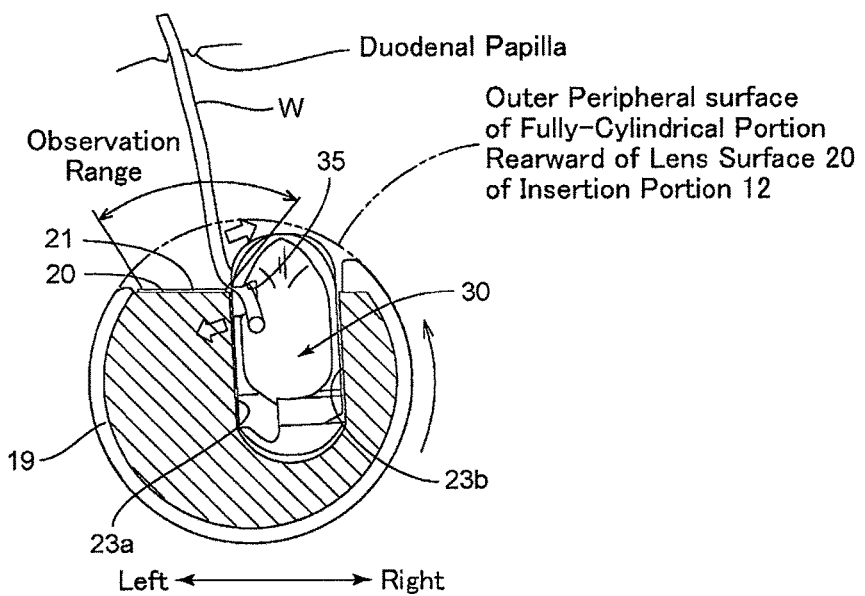
FIG. 7 is a cross-sectional view similar to that of FIG. 4, showing a state in which the insertion portion has been returned to the positional state of FIG. 4 from the positional state of FIG. 5.

The above-described raising base 30 is rotatable between the non-raised position shown in FIGS. 2 and 4 relative to the distal-end rigid portion 19 (raising-base accommodation recess 23) and the raised position (rearwardly tilting position) shown in FIGS. 7 and 8. When the raising base 30 is positioned at the non-raised position, the entire raising base 30 is positioned within the raising-base accommodation recess 23 (see FIG. 2; the pair of left and right raising-base side walls 34 of the raising base 30 oppose, in the leftward/rightward direction, the left inner surface 23a and the right inner surface 23b of the raising-base accommodation recess 23). If the raising base 30 is rotated toward the raised position from a predetermined position, part (distal end portion) of the raising base 30 protrudes upwardly from the lens mounting surface 20 (the upper edge of the right inner surface 23b) (see FIG. 6), and when the raising base 30 is rotated to the maximum raised position (the position in FIG. 8), the upward protrusion amount of the raising base 30 from the lens mounting surface 20 becomes maximum. However, when the raising base 30 is positioned at any position between the non-raised position and the raised position (see FIGS. 5 and 7), the raising base 30 is positioned within the inner peripheral side from the outer peripheral surface of a fully cylindrical portion positioned rearwardly from the lens mounting surface 20 of the insertion portion 12. Accordingly, even if the insertion portion 12 were to be advanced/retracted within a lumen of a patient with the raising base 30 positioned at a raised position or at the maximum raised position, there is little chance of the raising base 30 coming in contact with the lumen wall.

Figure 5:
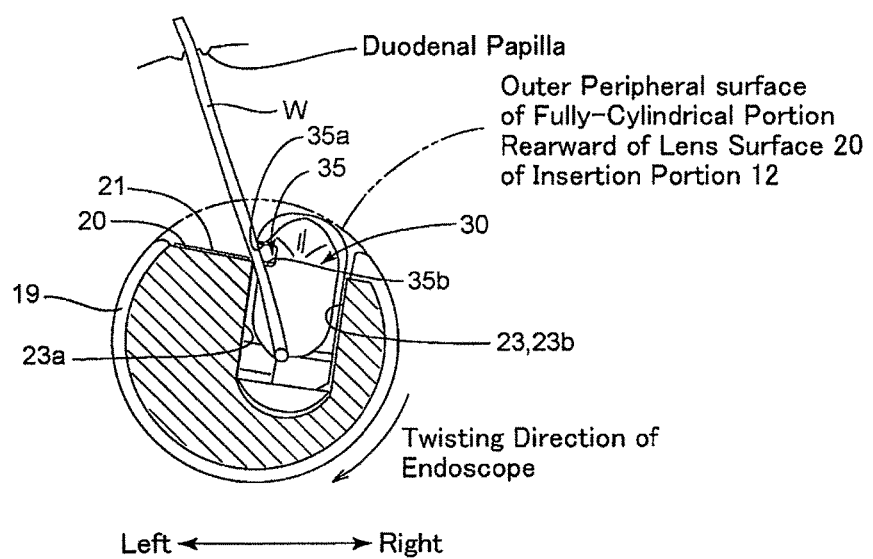
FIG. 5 is a cross-sectional view similar to that of FIG. 4, showing a state in which the insertion portion has been rotated in one direction about the axis thereof from the state shown in FIG. 2 and FIG. 4.
Figure 6:
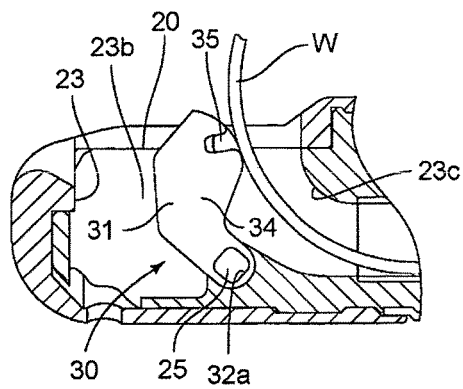
FIG. 6 is a longitudinal cross-sectional view similar to that of FIG. 2, showing a state where the raising base is positioned at a maximum raised position.

As shown in FIGS. 4, 5 and 7, slight gaps (clearances) exist between the left inner surface 23a of the raising-base accommodation recess 23 and the left raising-base side wall 34 of the raising base 30, and between the rightward inner surface 23b of the raising-base accommodation recess 23 and the right raising-base side wall 34 of the raising base 30. The size of the slight gaps are considerably smaller than the outer diameter of the guidewire W (cross-sectional diameter). A metal control wire extending in the forward/rearward direction is provided within the control body 11 and the insertion portion 12 and can advance and retract in the forward and rearward directions. The rear end of the control wire is connected to a raising-base control lever (controller; not shown in the drawings) provided on the control body 11, and the front end of the control wire is fit-engaged onto the wire-locking hole of the raising base 30. When the raising-base control lever is positioned at the non-raised position, the raising base 30 is positioned at the non-raised position. When the control wire is pulled rearwardly by the raising-base control lever being rotatably operated toward the maximum raised position, the raising base 30 gradually rotates toward the raised position, and when the raising-base control lever is rotated to the maximum raised position, the raising base 30 rotates to the maximum raised position. Furthermore, if the raising-base control lever is returned toward the non-raised position after the raising base 30 has been rotated toward the raised position, the raising base 30 rotates toward the non-raised position by the control wire sliding in the forward direction.

The locking operation of the above-described guidewire W is carried out by the raising base 30 in the following manner. Upon the raising base 30 being rotated in a direction toward the raised position with the insertion portion 12 (distal-end rigid portion 19) rotated about the axis thereof, since the inner-to-outer communicably-connected groove 35 becomes parallel with the lens mounting surface 20 at the close proximity of the raised position of the raising base 30 and at least the groove wall 35a, which is farther from the rotational shaft 25, is positioned above the lens mounting surface 20, an intermediate portion of the guidewire W that is in contact with a contact portion (corner) between the left inner surface 23a of the raising-base accommodation recess 23 and the lens mounting surface 20 is guided into the inner-to-outer communicably-connected groove 35 (see FIGS. 7 through 9). In this state, the operator rotates the raising-base control lever to the maximum raised position to thereby rotate the raising base 30 to the raised position. Furthermore, by returning the insertion portion 12 (distal-end rigid portion 19) to the original rotational position about the axis thereof, the guidewire W can be supported by being frictionally engaged with the groove walls 35a and 35b (the inner edge 35b1 and the outer edge 35a2 in particular) without contacting the left inner surface 23a or the rightward inner surface 23b of the raising-base accommodation recess 23. In other words, the groove wall 35b (the inner edge 35b1 in particular) and the groove wall 35a (the outer edge 35a2 in particular) of the inner-to-outer communicably-connected groove 35 are frictionally engaged with the guidewire W and function as locking surfaces (edges).

FIG. 8 shows a state in which the guidewire W has been correctly engaged with the inner-to-outer communicably-connected groove 35 of the raising base 30. The raising base 30 has been rotated in a direction toward the maximum raising position, shown by arrow A1, at which the guidewire W is pushed against by the curved surface 23c of the raising-base accommodation recess 23 by a force shown by arrow A2, and applies a rotational force in the direction shown by arrow A3 against the raising base 30 via the inner-to-outer communicably-connected groove 35. At this stage, the guidewire W is frictionally engaged with the groove wall 35b (the inner edge 35b1 in particular) and the groove wall 35a (the outer edge 35a2 in particular) of the inner-to-outer communicably-connected groove 35.

Figure 10:
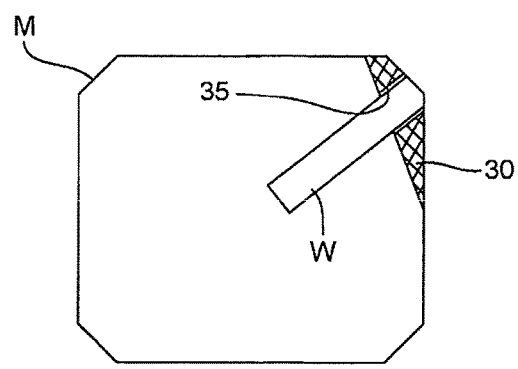
FIG. 10 shows a monitor screen of when the raising base is rotated to the raised position in a state where the guidewire has fully engaged with an inner-to-outer communicably connected groove, which communicably connects the inner side of a treatment tool support groove with the outer side thereof.
Figure 11:
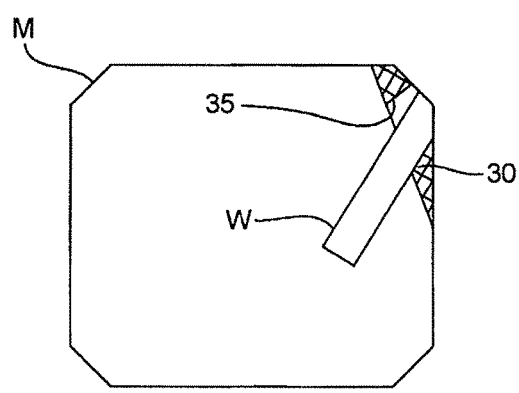
FIG. 11 shows a monitor screen of when the raising base is rotated to the raised position in a state where the guidewire has either not engaged or not fully-engaged with an inner-to-outer communicably connected groove, which communicably connects the inner side of the treatment tool support groove with the outer side thereof.
Figure 12:
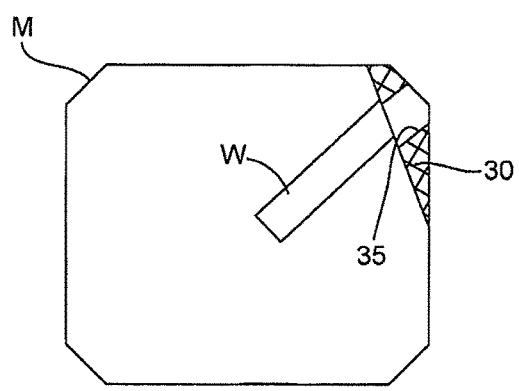
FIG. 12 shows a monitor screen of when the raising base is rotated to the raised position in a state where the guidewire is engaged with the treatment tool support groove.

The gist of the observation and treatment of pancreatic and bile ducts using the above-described endoscope 10 will be described hereinbelow. First the connector body 14 of the endoscope 10, in which the raising base 30 is positioned at the non-raised position, is connected to the aforementioned processor, and a light source that is built into the processor is illuminated. Thereafter, since illumination light generated by the light source is supplied to the rearward end of the light-guide fiber, and is further supplied to the illumination lens element 22 from the front end of the light-guide fiber, the illumination light externally emits from the distal-end rigid portion 19 via the illumination lens element 22. Furthermore, an observed image that is observed through the objective lens element 21 is captured by the aforementioned image sensor (the observation range of the objective lens element 21 is shown in FIGS. 4 and 7), and the observation-image data generated by the image sensor is transmitted to the processor via the image-signal cable. Imaging processing is performed on the observation-image data, which has been transmitted to the processor, by an image processor that is built into the processor, and thereafter, is displayed on a CRT monitor screen M (FIGS. 10 through 12). The operator inserts the distal end of the insertion portion 12 into the duodenum via the patient's mouth, esophagus and stomach, while observing an image displayed on the CRT monitor screen M. Furthermore, the objective lens element 21 is made to face the duodenal papilla by positioning the raising-base accommodation recess 23 (raising base 30) at the close proximity, of the duodenal papilla (see FIGS. 4, 5 and 7) and rotating the insertion portion 12 (distal-end rigid portion 19) about the axis thereof, so that the duodenal papilla is displayed at the central area of the CRT monitor screen M. Thereafter, the operator inserts a flexible catheter (not shown in the drawings) into the treatment-tool insertion tube 26 from the treatment-tool insertion port protrusion 11a of the endoscope 10, projects the distal end of the catheter into the raising-base accommodation recess 23 via the distal-end opening of the treatment-tool insertion tube 26, and the distal end of the catheter is projected toward the outer peripheral side of the raising-base accommodation recess 23 (distal-end rigid portion 19) while the distal-end proximity of the catheter contacts the treatment-tool support groove 33 of the raising base 30. At this stage, since the base wall 35c of the inner-to-outer communicably-connected groove 35 is positioned at a higher position than that of the U-cross-sectional shaped base portion 33a of the raising base 30, there is little chance of the catheter, which is inserted along the base portion 33a, catching on an edge of the base wall 35c, so that a smooth insertion can be carried out. Furthermore, the raising-base control lever that is positioned at the non-raised position is operated to rotate toward the maximum raised position to rotate the raising base 30 toward the maximum raised position, and the distal end of the catheter is inserted into the duodenal papilla by pushing (relatively moving) the catheter out from the distal end of the treatment-tool insertion tube 26. Subsequently, a contrast agent is injected so that the bile duct or the pancreatic duct can be observed by radioscopy.

Subsequently, the flexible metal guidewire W is inserted inside the catheter from the opening on the control body 11 side of the catheter, the distal end of the guidewire W is projected from the opening of the catheter at the distal end thereof, and the distal end of the guidewire W is inserted into the duodenal papilla (see FIG. 4). Thereafter, the distal end of the guidewire W is inserted until a desired location in the bile duct or the pancreatic duct while the bile duct or the pancreatic duct is observed by radioscopy. In this state, by combining the above-described raising operation of the raising base 30 with the rotating operation of the insertion portion 12 (distal-end rigid portion 19) about the axis thereof, the guidewire W is locked onto the raising base 30. Subsequently, with the guidewire W inserted into the duodenal papilla, the operator pulls out the catheter from the treatment-tool insertion tube 26 and the treatment-tool insertion port protrusion 11a (and also the patient's lumen) along the guidewire W while manually grasping the base portion of the catheter (the portion thereof that externally protrudes from the treatment-tool insertion port protrusion 11a). Since the guidewire W is locked onto the raising base 30, the guidewire W does not come out with the catheter. Subsequently, the base portion of the guidewire W (the portion externally protruding from the treatment-tool insertion port protrusion 11a) is inserted into a distal end (internal space) of a treatment tool (omitted from the drawings), which is a flexible longitudinal tubular member. Thereafter, the distal end of the treatment tool is inserted into the treatment-tool insertion tube 26 along the guidewire W, the distal end of the treatment tool that externally projects from the raising-base accommodation recess 23 is inserted to a desired location in the bile duct or the pancreatic duct via the duodenal papilla, and a predetermined treatment is performed on the bile duct or the pancreatic duct with the treatment tool.

Upon the treatment, using the treatment tool, ending, the treatment tool is pulled out from the treatment-tool insertion tube 26 and the treatment-tool insertion port protrusion 11a of the endoscope 10 (and the patient's lumen) along the guidewire W. In this pulling out operation, first the operator pulls the entire treatment tool in the proximal direction (toward the treatment-tool insertion port protrusion 11a) while manually grasping the base portion of the treatment tool (the portion externally protruding from the treatment-tool insertion port protrusion 11a), and the distal end of the treatment tool is rearwardly moved relative to the raising-base accommodation recess 23 to thereby be drawn into the treatment-tool insertion tube 26. Subsequently, in a state where the raising base 30 has returned to the non-raised position (see FIG. 4), the operator, for example, rotates the insertion portion 12 (distal-end rigid portion 19) about the axis thereof while viewing the CRT monitor screen M, moves an intermediate portion of the guidewire W leftward relative to the raising base 30 to thereby engage the intermediate portion of the guidewire W onto the inner-to-outer communicably-connected groove 35 of the raising base 30 and make the intermediate portion contact a contact portion (corner) between the left inner surface 23a and the lens mounting surface 20 (see FIG. 5). Furthermore, by rotating the raising-base control lever toward the maximum raised position, the raising base 30 is rotated toward the maximum raised position. Subsequently, the intermediate portion of the guidewire W is bent rearwardly by the raising base 30 (raising-base side walls 34) (see FIG. 6).

Furthermore, at this stage, part of the raising base 30, part of the inner-to-outer communicably-connected groove 35 and part of the guidewire W enter into the observation range (observation field-of-view) of the objective lens element 21. In other words, as shown in FIG. 10, part of the raising base 30, part of the inner-to-outer communicably-connected groove 35 and part of the guidewire W are displayed on the CRT monitor screen M. Note that if the guidewire W is not engaged into the inner-to-outer communicably-connected groove 35 (or not completely engaged), part of the raising base 30, part of the inner-to-outer communicably-connected groove 35 and part of the guidewire W are displayed on the CRT monitor screen M in the manner shown in FIG. 11 (in which part of the outer periphery of the inner-to-outer communicably-connected groove 35 is covered by the guidewire W), or if the guidewire W is engaged with the treatment-tool support groove 33 instead of the inner-to-outer communicably-connected groove 35, part of the raising base 30, part of the inner-to-outer communicably-connected groove 35 and part of the guidewire W are displayed on the CRT monitor screen M in the manner shown in FIG. 12 (which shows the guidewire W not engaged with the inner-to-outer communicably-connected groove 35). Hence, since the operator can visually discern whether or not the guidewire W has completely engaged with the inner-to-outer communicably-connected groove 35 upon rotating the raising base 30 to the raised position, the operator can rotate the insertion portion 12 (distal-end rigid portion 19) in the reverse direction while viewing the CRT monitor screen M to attain the state shown in FIG. 7 (the rotational position of the insertion portion 12 (distal-end rigid portion 19) about the axis thereof is moved to the same position as that of FIG. 4 to display the duodenal papilla at the central portion of the CRT monitor screen M).

Accordingly, in this state, when the operator pulls the treatment tool, which is inserted into the treatment-tool insertion tube 26, along the guidewire W, even if a large frictional force were to occur between the inner peripheral surface of the treatment tool and the outer peripheral surface of the guidewire W, there is little risk of the guidewire W being unintentionally pulled from the treatment-tool insertion tube 26 and out from the treatment-tool insertion port protrusion 11a. Therefore, the operator can smoothly pull out the treatment tool along the guidewire W and out of the treatment-tool insertion port protrusion 11a. Furthermore, since the outer diameter of the guidewire W is smaller than the width and depth of the inner-to-outer communicably-connected groove 35, and the groove wall 35a of the inner-to-outer communicably-connected groove 35 is positioned above the lens mounting surface 20 (the upper edge of the rightward inner surface 23b) upon the raising base 30 rotating to the raised position (since the groove wall 35a does not face the left inner surface 23a in the leftward/rightward direction), the guidewire W does not get clasped in between the raising base 30 and the left inner surface 23a when the raising base 30 is rotated to the raised position. Furthermore, the guidewire W does not get clasped between the raising base 30 and the curved surface 23c. Accordingly, (so long as the outer diameter of the guidewire W is a size that is engagable with the inner-to-outer communicably-connected groove 35) since the force applied on the guidewire W via the locking edge of the inner-to-outer communicably-connected groove 35 when the raising base 30 is rotated to the raised position does not become excessive, regardless of the diameter size of the guidewire W and the rotational angle of the raising base 30, the guidewire W is not broken by the inner-to-outer communicably-connected groove 35 (raising base 30).

After the treatment tool is externally pulled out of the endoscope 10, in the case where another treatment is carried out on the bile duct or the pancreatic duct, another flexible tubular treatment tool (omitted from the drawings), which is different from the above-mentioned treatment tool, is inserted along the guidewire W into the bile duct or the pancreatic duct, and a necessary treatment is carried out on the bile duct or the pancreatic duct using this other treatment tool. Upon completion of the treatment on the bile duct or the pancreatic duct, the guidewire W is externally pulled out of the treatment-tool insertion port protrusion 11a while the base portion of the guidewire W (the portion that protrudes out from the treatment-tool insertion port protrusion 11a) is manually grasped, the raising-base control lever is rotated to the non-raised position to return the raising base 30 to the non-raised position, and thereafter the insertion portion 12 is pulled out from inside the body of the patient.

FIGS. 13 through 16 respectively show second, third, fourth and fifth embodiments of the raising base 30 that is used in the endoscope of the present invention. The differences between these embodiments and the embodiment shown in FIGS. 1 through 12 are the features surrounding the inner-to-outer communicably-connected groove 35 formed in the raising base 30; hence, only the features regarding the raising base 30 will be discussed hereinbelow.

Figure 13:
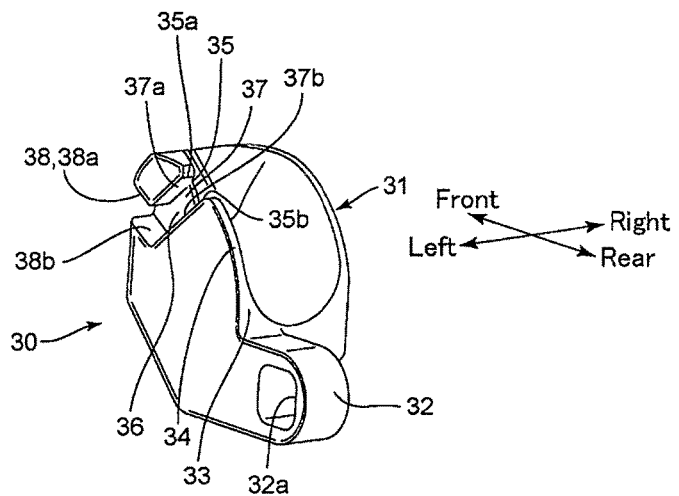
FIG. 13 is a rear perspective view of a second embodiment of the raising base according to the present invention.

In the embodiment shown in FIG. 13, similar to the first embodiment, the inner-to-outer communicably-connected groove 35, which communicably connects the inner side of the treatment-tool support groove 33 with the outer side thereof, is formed on the left raising-base side wall 34 of the body portion 31 of the raising base 30, however, a guidewire support groove 36, having an L-shape in a side elevational view, is formed as a bottomed groove continuously with the inner-to-outer communicably-connected groove 35 on the outer surface of this raising-base side wall 34 (on the surface that opposes the left inner surface 23a of the raising-base accommodation recess 23). The guidewire support groove 36 is provided with an intersecting portion 37 which extends linearly, and an orthogonal portion 38 which extends linearly and intersects with the intersecting portion 37 at a front end of the intersecting portion 37. The intersecting portion 37 and the orthogonal portion 38 are communicably connected with each other. The rear end of the intersecting portion 37 (an end portion/an end positioned at the distal-end opening of the treatment-tool insertion tube 26 when the raising base 30 is positioned at the raised position) and the opposite end of the orthogonal portion 38 to that of the intersecting portion 37 are open. The cross-sectional shape of the intersecting portion 37 and the orthogonal portion 38 are both substantially rectangular (see FIG. 5). Upper and lower portions of the inner surface of the intersecting portion 37 are mutually parallel while extending in a longitudinal direction (one direction) of the intersecting portion 37 and define a pair of opposing inner surfaces 37a and 37b, which oppose each other in a direction orthogonal to the leftward/rightward direction (the widthwise direction of the insertion portion 12) and the longitudinal direction of the intersecting portion 37. Whereas, the orthogonal portion 38 is provided, on the inner surfaces thereof, with an opposing inner surface 38a which is continuous with the opposing inner surface 37a and an opposing inner surface 38b which is continuous with the opposing inner surface 37b, respectively. The opposing inner surface 38a and the opposing inner surface 38b are mutually parallel while extending in a longitudinal direction of the orthogonal portion 38 and oppose each other in a direction orthogonal to the leftward/rightward direction (the widthwise direction of the insertion portion 12) and the longitudinal direction of the orthogonal portion 38. The widths of the intersecting portion 37 and the orthogonal portion 38 (the space between the opposing inner surface 37a and the opposing inner surface 37b, and the space between the opposing inner surface 38a and the opposing inner surface 38b) and the depth (leftward/rightward dimensions) of the guidewire support groove 36 are larger than the outer diameter of the guidewire W and are smaller than the outer diameters of the catheter and the treatment tool that are discussed later (the catheter and the treatment tool cannot engage with the guidewire support groove 36). When the raising base 30 is rotated to the raised position, the entirety of the orthogonal portion 38 and part of the intersecting portion 37 (the portion on the orthogonal portion 38 side) are positioned above the lens mounting surface 20 (the upper edge of the rightward inner surface 23b) (so as to no longer oppose the left inner surface 23a in the leftward/rightward direction), and the entire guidewire support groove 36 is positioned above the treatment-tool insertion tube 26.

Figure 14:
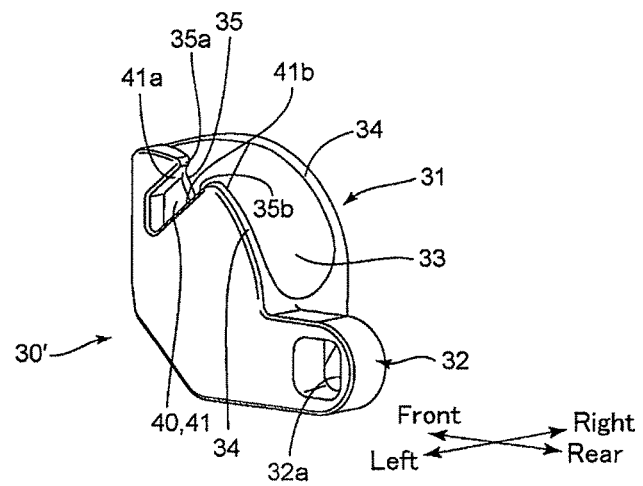
FIG. 14 is a rear perspective view of a third embodiment of the raising base according to the present invention.

Also in the third embodiment shown in FIG. 14, the inner-to-outer communicably-connected groove 35, which communicably connects the inner side of the treatment-tool support groove 33 with the outer side thereof, is formed on the left raising-base side wall 34 of a raising base 30'. Furthermore, a guidewire support groove 40, which is linear in shape in a side elevational view, is formed as a bottomed groove on the outer surface (the surface opposing the left inner surface 23a of the raising-base accommodation recess 23) of this raising-base side wall 34 and is continuous with the inner-to-outer communicably-connected groove 35.

The guidewire support groove 40 is only provided with an intersecting portion 41 which extends linearly, and the end of the intersecting portion 41 opposite to the inner-to-outer communicably-connected groove 35 is closed. The cross-sectional shape of the intersecting portion 41 is substantially rectangular. Upper and lower portions of the inner surface of the intersecting portion 41 are mutually parallel while extending in a longitudinal direction (one direction) of the intersecting portion 41 and define a pair of opposing inner surfaces 41a and 41b, which oppose each other in a direction orthogonal to the leftward/rightward direction (the widthwise direction of the insertion portion 12) and the longitudinal direction of the intersecting portion 41. The width of the intersecting portion 41 (the space between the opposing inner surface 41a and the opposing inner surface 41b) and the depth (leftward/rightward dimensions) of the intersecting portion 41 are larger than the diameter of the guidewire W and are smaller than the outer diameters of the catheter and the treatment tool that are discussed later (the catheter and the treatment tool cannot engage with the guidewire support groove 40). When the raising base 30' is rotated to the raised position, part (the upper part) of the guidewire support groove 40 (intersecting portion 41) is positioned above the lens mounting surface 20 (the upper edge of the rightward inner surface 23b) (so as to no longer oppose the left inner surface 23a in the leftward/rightward direction).

Figure 15:
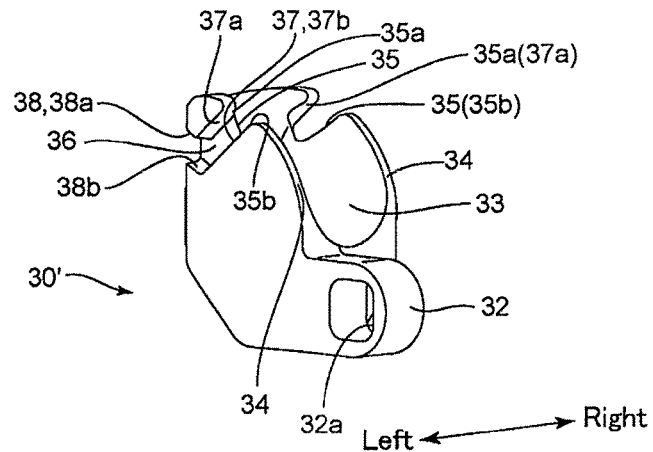
FIG. 15 is a rear perspective view of a fourth embodiment of the raising base according to the present invention.
Figure 16:
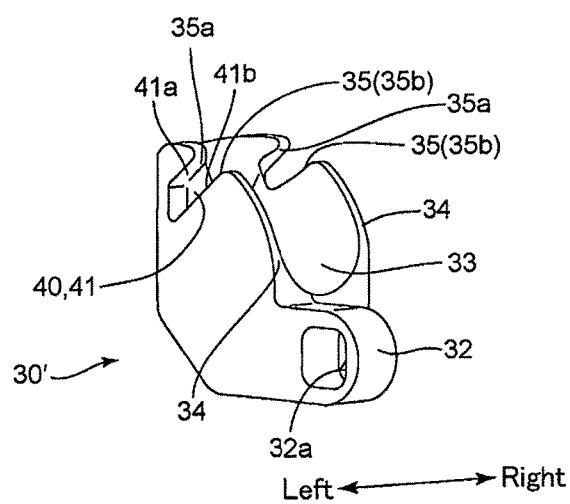
FIG. 16 is a rear perspective view of a fifth embodiment of the raising base according to the present invention.

In the fourth embodiment of FIG. 15, the inner-to-outer communicably-connected groove 35, which communicably connects the inner side of the treatment-tool support groove 33 with the outer side thereof, and the guidewire support groove 36 are formed on each of left and right the raising-base side walls 34 of the raising base 30'. In the fifth embodiment shown in FIG. 16, the inner-to-outer communicably-connected groove 35 and the guidewire support groove 40 are formed on each of left and right the raising-base side walls 34 of the raising base 30'. By forming two sets of the inner-to-outer communicably-connected groove 35 and the guidewire support groove 36 or 40 on a single raising base 30 or 30' in this manner, the guidewire W can be easily engaged with the guidewire support groove 36 or 40 when the raising base 30 or 30' is rotated to the raised position.

The operation of the inner-to-outer communicably-connected groove 35 in the embodiments of FIGS. 13 through 16 is the same as the operation of the inner-to-outer communicably-connected groove 35 described in the embodiment of FIGS. 1 through 12. Namely, the angle θ defined by the inner-to-outer communicably-connected groove 35 and the lens mounting surface 20 gradually reduces during the movement of the raising base 30 from the non-raised position to the raised position to become substantially parallel with the lens mounting surface 20; and when the inner-to-outer communicably-connected groove 35 is parallel with the lens mounting surface 20, at least the groove wall 35a which is farther from the rotational shaft 25 is positioned above the lens mounting surface 20. Accordingly, by combining the raising operation of the raising base 30 with the rotational movement of the insertion portion 12 about the axis thereof, the guidewire W can be guided into the inner-to-outer communicably-connected groove 35, be frictionally engaged with the groove walls 35a and 35b (the inner edge 35b1 and the outer edge 35a2 in particular), and be supported thereby.

In the above-described embodiments, a description is given in which, out of the groove wall 35b and the groove wall 35a of the inner-to-outer communicably-connected groove 35 (which communicably connects the inner side of the treatment-tool support groove 33 with the outer side thereof), the inner edge 35b1 and the outer edge 35a2 in particular function as edges with which the guidewire W frictionally engages and locks onto; however, the thickness of the raising-base side wall 34 can be made thinner, so that sometimes it is difficult to form edges on both sides of the raising-base side wall 34, with respect to the thickness direction thereof. In such a configuration, it is possible for the guidewire W to lock onto (the entirely of each of) the groove wall 35b and the groove wall 3a.

The above embodiments and modified embodiments apply the present invention to a side-viewing endoscope 10, however, the present invention can also be applied to an oblique-viewing endoscope. Furthermore, a site other than pancreatic or bile ducts can be observed and treated, depending on the endoscope.

INDUSTRIAL APPLICABILITY

It is desirable for the endoscope provided with a raising base according to the present invention to be applied to, e.g., an endoscope for performing various treatments by guiding a treatment tool to pancreatic or bile ducts using a guidewire.

REFERENCE SIGNS LIST

10 Endoscope
11 Control body
11a Treatment-tool insertion port protrusion
11b Cap
12 Insertion portion
13 Universal tube
14 Connector body
15 Bending-control lever
17 Bendable portion
18 Flexible tubular portion
19 Distal-end rigid portion
20 Lens mounting surface
21 Objective lens element
22 Illumination lens element
23 Raising-base accommodation recess
23a Left inner surface
23b Rightward inner surface
23c Curved surface (wire contacting portion)
25 Rotational shaft
26 Treatment-tool insertion tube (treatment-tool insertion conduit)
30 30' Raising base
31 Body portion
32 Supported portion
32a Pivotal support hole
33 Treatment-tool support groove
33U U-shaped groove
33V V-shaped groove
33a Base portion
34 Raising-base side walls 35 Inner-to-outer communicably-connected groove
35a 35b Groove wall
35a1 Inner edge
35a2 Outer edge (locking edge)
35b1 Inner edge (locking edge)
35b2 Outer edge
35c Base wall
37 Intersecting portion
37a 37b Opposing inner surface
38 Orthogonal portion
38a 38b Opposing inner surface
40 Guidewire support groove
41 Intersecting portion
41a 41b Opposing inner surface
M CRT monitor screen
W Guidewire

The invention claimed is:

1. An endoscope provided with a raising base comprising:
a control body;
an insertion portion extending from said control body;
a raising-base accommodation recess formed in a distal-end proximal portion of said insertion portion;
a treatment-tool insertion conduit formed in said insertion portion, a distal-end opening of said treatment-tool insertion conduit being communicably connected with said raising-base accommodation recess, and a flexible longitudinal treatment tool and guidewire being insertable through said treatment-tool insertion conduit;
a raising base provided in said raising-base accommodation recess, said raising base being rotatable between a non-raised position and a raised position about a rotational shaft extending in a widthwise direction of said insertion portion, wherein said raising base includes a treatment-tool support groove which extends in a direction extending from said insertion portion; a pair of raising-base side walls positioned on either side of said treatment-tool support groove and opposing left and right surfaces of said raising-base accommodation recess in said widthwise direction of said insertion portion; and
an inner-to-outer communicably-connected groove provided on at least one of said pair of raising-base side walls, said inner-to-outer communicably-connected groove being formed as a through-groove in a direction of said rotational shaft and formed as a groove having a bottom and that extends in a depth direction of said treatment-tool support groove, said inner-to-outer communicably-connected groove comprising a pair of mutually opposing parallel groove walls comprising a first groove wall and a second groove wall, the first groove wall being farther from the rotational shaft than the second groove wall, and said inner-to-outer communicably-connected groove communicably connecting an inner side of said treatment-tool support groove with an outer side thereof,
wherein said inner-to-outer communicably-connected groove is engagable with said guidewire and is not engagable with said treatment tool, and
wherein, when said raising base is positioned at said raised position, said inner-to-outer communicably-connected groove frictionally engages with said guidewire, with said guidewire guided into said inner-to-outer communicably-connected groove, without causing said guidewire to contact a left and right inner wall surface of said raising-base accommodation recess.

2. The endoscope provided with the raising base according to claim 1, wherein opposing edges of said mutually opposing parallel groove walls are configured to frictionally engage with said guidewire.

3. The endoscope provided with the raising base according to claim 1, said pair of raising-base side walls of said raising base define, as a whole, a U-shaped cross section on a portion of said raising-base side walls on which said inner-to-outer communicably-connected groove exists, and
wherein a base wall of said inner-to-outer communicably-connected groove is positioned above a base portion of said treatment-tool support groove a direction of depth of said treatment-tool support groove.

4. The endoscope provided with the raising base according to claim 1, wherein said inner-to-outer communicably-connected groove is provided on each of said pair of raising-base side walls of said raising base.

5. The endoscope provided with the raising base according to claim 1, wherein an objective lens element is provided on an outer peripheral surface of said insertion portion,
wherein at least part of said inner-to-outer communicably-connected groove is positioned within an observational field-of-view of said objective lens element when said raising base is positioned at said raised position.

* * * * *